United States Patent [19]

Schoots

[11] 4,332,253
[45] Jun. 1, 1982

[54] DISPOSABLE DIAPER AND TOP SHEET THEREFOR

[75] Inventor: Peter J. Schoots, Walpole, Mass.

[73] Assignee: The Kendall Company, Boston, Mass.

[21] Appl. No.: 140,616

[22] Filed: Apr. 15, 1980

[51] Int. Cl.³ .......................................... A61F 13/16
[52] U.S. Cl. .................................. 128/287; 128/284;
526/328.5; 428/286; 428/287; 428/288;
428/290
[58] Field of Search ........................... 128/287, 284;
526/328.5; 260/29.6 E

[56] References Cited
U.S. PATENT DOCUMENTS

| 2,270,024 | 1/1942 | Renfrew et al. | 526/328.5 |
| 3,299,010 | 1/1967 | Samour | 428/355 |
| 3,489,148 | 1/1970 | Duncan et al. | 128/284 |
| 3,563,242 | 2/1971 | Hedstrom et al. | 128/287 |
| 3,925,442 | 12/1975 | Samou | 260/459 R |
| 3,926,891 | 12/1975 | Gross et al. | 260/29.6 E |

Primary Examiner—George F. Lesmes
Assistant Examiner—B. K. Johnson

[57] ABSTRACT

An absorbent pad such as a disposable diaper having a water-resistant backing sheet, a layer of absorbent material, and a top sheet in the form of a fibrous web with a binder of polymeric material containing at least 1% by weight of combined 2-ethyl hexyl acrylate.

8 Claims, 2 Drawing Figures

FIG 1
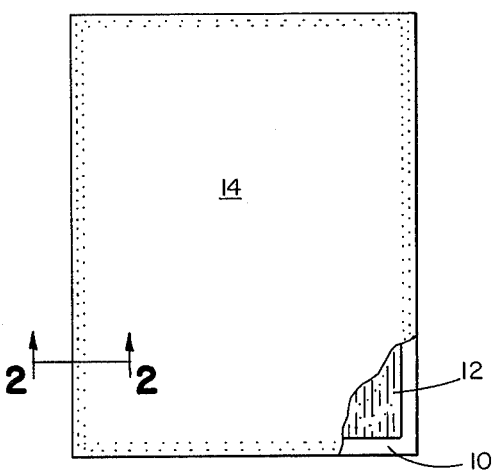
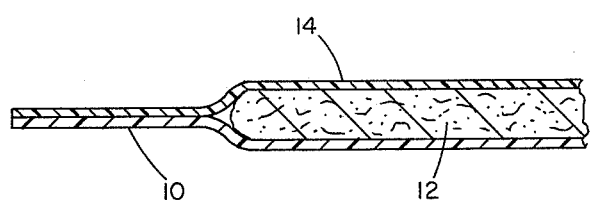
FIG 2

DISPOSABLE DIAPER AND TOP SHEET THEREFOR

This invention relates to absorbent pads such as disposable diapers and the like for use in contact with the skin and pertains more specifically to a top sheet (or face sheet) for use in such absorbent pads providing greatly improved dryness properties with little or no increase in strike through time.

Absorbent pads such as disposable diapers customarily comprise a water-resistant backing sheet, a layer of absorbent material, and a liquid pervious top sheet (or face sheet), the top sheet being arranged to be placed in contact with the body or skin or an individual.

Important characteristics of the top sheets of such absorbent pads are that they delay or minimize passage of aqueous liquid such as urine from the layer of absorbent material, after saturation, through the top sheet to the external surface thereof (i.e., that they and the pads of which they form a part exhibit high "dryness"), while at the same time they provide fast initial passage of an aqueous liquid such as urine from outside the pad in the reverse direction through the top sheet into the layer of absorbent material (i.e., that they and the pads of which they form a part exhibit short "strike through" time). In addition, it is highly desirable that top sheets of such absorbent pads be flexible and possess a soft hand, and that they exhibit acceptable strength when they are wet.

In the past it has been customary to provide top sheets in the form of one or more non-woven fibrous webs of textile fibrous material such as polyester, rayon, polyamide, polypropylene or the like fibers together with a binder of water insoluble polymeric material serving to bond the fibers together, and to ensure adequate dryness properties by employing a top sheet of high weight.

It has now been found that the dryness of such top sheets and of absorbent pads in which they are present is significantly improved by including in the polymeric binder composition at least 1%, by weight of the total polymeric binder, of combined 2-ethyl hexyl acrylate, preferably from 3 to 30% by weight. The combined 2-ethyl hexyl acrylate may be present as a homopolymer which is mixed with the remaining polymeric binder, or it may be present as a copolymer of 2-ethyl hexyl acrylate with one or more other polymerizable monomers containing a polymerizable ethylenic unsaturation. Consequently the binder may include simply a single copolymer of 2-ethyl hexyl acrylate with one or more other copolymerizable ethylenically unsaturated monomers, or it may include a mixture of such a copolymer with one or more other polymers or copolymers of other polymerizable ethylenically unsaturated monomers, or it may include a mixture of a homopolymer of 2-ethyl hexyl acrylate with one or more homopolymers or copolymers of other polymerizable ethylenically unsaturated monomers, provided that the total weight of combined 2-ethyl hexyl acrylate amounts to at least 1% of the total weight of polymeric binder, preferably from 3 to 30% by weight.

Among the preferred other polymerizable ethylenic monomers with which 2-ethyl hexyl acrylate can be copolymerized are lower alkyl acrylates in which the alkyl groups contain 1 to 5 carbon atoms such as ethyl acrylate or butyl acrylate, vinyl acetate or vinyl propinate, acrylonitrile, vinyl chloride, styrene, acrylic or methacrylic acid, or the like. The same polymerizable ethylenic monomers can be homopolymerized or copolymerized with each other and mixed with a homopolymer or copolymer of 2-ethyl hexyl acrylate to form a binder suitable for use in the present invention. It is preferred when a homopolymer or copolymer of 2-ethyl hexyl acrylate is blended with a conventional polymer or copolymer (free from 2-ethyl hexyl acrylate) to form the binder, that the first homopolymer or copolymer contain at least 50% by weight of combined 2-ethyl hexyl acrylate. When a copolymer of 2-ethyl hexyl acrylate with another copolymerizable ethylenic monomer is used as the sole polymer in the binder, it is preferred that it contain at least 1% of combined 2-ethyl hexyl acrylate. In one preferred embodiment the polymeric binder comprises a copolymer of an alkyl acrylate in which the alkyl group contains from 1 to 5 carbon atoms with 2-ethyl hexyl acrylate. In another preferred embodiment the polymeric binder comprises a copolymer of an alkyl acrylate in which the alkyl group contains from 1 to 5 carbon atoms with vinyl acetate and with 2-ethyl hexyl acrylate. In other preferred embodiments the polymeric binder comprises a copolymer of butyl acrylate or of a mixture of butyl and ethyl acrylate with vinyl acetate and with 2-ethyl hexyl acrylate. The total polymeric binder present in the top sheet is at least 15% by weight of the entire top sheet including the fibrous web, preferably from 20 to 50% by weight of the total top sheet. The total top sheet weighs from 10 to 30 grams per square yard.

In the drawing,

FIG. 1 is a plan view of a disposable diaper embodying a top sheet of the present invention; and FIG. 2 is a view in section partly broken away taken along line 2—2 of FIG. 1.

As shown in the drawing, the disposable diaper includes a top sheet 10, a layer of absorbent material 12, and water resistant backing sheet 14, sheets 10 and 14 being bonded together around the periphery of the diaper in the usual manner. Any conventional layer of absorbent material can be used, as well as any conventional water resistant backing sheet.

The top sheet 10 in the present invention comprises one or more webs of any natural or synthetic textile fibers such as rayon, polyamide, polyester, polypropylene, or the like, polyester fibers being preferred; along with the web is employed a polymeric binder composition containing at least 1% by weight of combined 2-ethyl acrylate. The combined 2-ethyl hexyl acrylate can be present in the form of a homopolymer or in the form of a copolymer with other monomers containing polymerizable ethylenic unsaturation, as described above.

The dryness and strike through characteristics of the top sheet of the present invention and of the absorbent pads incorporating it are measured by conventional test procedures well known to those skilled in the art. To determine strike through time, a sample of the top sheet to be tested is placed on top of a layer of absorbent material, and a measured amount of synthetic urine solution (20 g sodium chloride and 5 g of octyl phenoxy polyethoxy (9-10) ethanol sold as Triton X-100 dissolved in 1990 ml of water) is deposited on top of the top sheet, and the time required for the solution to pass through the top sheet is measured. After measuring the strike through time, additional measured amounts of the solution are passed through the top sheet into the layer of absorbent material. A weight of 8 lb. is then placed on the upper surface of the top sheet for 3 minutes, after which the weight is removed. Two pieces of filter paper of known weight are placed on the upper surface of the top sheet, the weight is replaced and allowed to remain for 2 minutes. The two pieces of filter paper are then removed and weighed to determine the amount of solution absorbed by the filter paper. This amount is defined as the dryness value of the top sheet.

EXAMPLES

In all examples, the fiber webs were made by carding polyester fibers into a web of 4-5 g/yd$^2$ weight. By combining three of such webs on a conveyor belt, a total web weight was obtained between 12 and 14 g/yd$^2$. This combined web was then saturated by passing the web through the nip of a gravure print roll and a rubber press roll. The gravure print roll, by rotating in a bath of formulated latex, delivers a controlled amount of binder to the fibrous web.

After passing through the nip of the print roll and the rubber roll, the saturated web was then dried for approximately 60 seconds at 320° F. In each case the finished top sheet contained approximately 65% by weight of polyester fibers and approximately 35% polymeric binder, the total weight of the sheet being 18-20 g/sq. yd.

Before testing, all fabrics were conditioned for at least one hour at 70° F. and 65% RH.

The latex formulation used as a control or standard was an aqueous dispersion containing about 15% by weight of a binder copolymer consisting of approximately 42% combined butyl acrylate and approximately 52% combined vinyl acetate by weight along with small amounts of N-methylol acrylamide and of acrylic acid; the dispersion also contained minor proportions of conventional emulsifying agents and of ammonium chloride. Similar products were prepared in the same way except that the aqueous dispersion of binder copolymer contained in addition varying amounts of a binder copolymer as described in U.S. Pat. No. 3,299,010 containing combined therein 65 parts by weight of 2-ethyl hexyl acrylate, 27.5 ethyl acrylate, 2.5 acrylonitrile, 1.0 acrylic acid and 4.0 Primene maleamic acid. The amounts of the second copolymer were such that the amounts of combined 2-ethyl hexyl acrylate in the total polymeric binder were as shown in the following table, the total binder in each case being approximately 35% by weight of the total sheet. The dryness of each top sheet as determined by the standard test described above was as shown in the table.

TABLE I

| Percent combined 2-ethyl hexyl acrylate in total binder | 0 | 0.65 | 3.25 | 6.5 |
|---|---|---|---|---|
| Dryness (g) | 0.84 | 0.72 | 0.34 | 0.20 |
| Strike through (sec) | 1.3 | 1.0 | 1.3 | 1.3 |

Other top sheets were prepared using the same procedure by adding to the control latex a copolymer latex containing in combined form 75 parts by weight 2-ethyl hexyl acrylate, 20 ethyl acrylate, 2.5 methyl acrylate, 2.5 acrylic acid and 2.25 of a monomer consisting of the mole to mole reaction product of maleic anhydride, dimethyl amino ethanol, and chloroacetamide, with which reaction product is mixed an equimolar amount of ammonium lauryl sulfate. The latter combination of monomer with ammonium lauryl sulfate serves as a dispersing agent for all of the monomers as well as for the finished polymer of which it forms a part, as described in Samour U.S. Pat. No. 3,925,442. The amounts of combined 2-ethyl hexyl acrylate in the total polymeric binder and the strike through and dryness of each top sheet were as follows:

TABLE II

| % combined 2-ethyl hexyl acrylate in total binder | 0 | 0.73 | 3.67 | 7.3 | 14.7 |
|---|---|---|---|---|---|
| Dryness (g) | 1.17 | .97 | .10 | .10 | .10 |
| Strike through (sec) | 1.0 | 1.1 | 1.1 | 1.2 | 5.9 |

Still other sheets were made by adding to the control latex a copolymer latex having in combined form 80 parts by weight 2-ethyl hexyl acrylate, 15.5 parts ethyl acrylate, 2.5 parts acrylonitrile, and 2.0 parts acrylic acid, and containing as a dispersing and stabilizing agent an alkylated bisulfonated diphenyl ether. The amounts of combined 2-ethyl hexyl acrylate in the total polymeric binder and the strike through and dryness of top sheets were as follows:

TABLE III

| % combined 2-ethyl hexyl acrylate in total binder | 0 | 0.8 | 4.0 | 8.0 |
|---|---|---|---|---|
| Dryness (g) | 1.0 | 0.33 | 0.22 | 0.14 |
| Strike through (sec) | 1.0 | 1.2 | 1.1 | 2.8 |

Other sheets were made, using the same procedures, by impregnating a polyester fiber web with different polymeric binders consisting solely of a copolymer containing butyl acrylate (BuAcr), vinyl acetate (VAc), 2-ethyl hexyl acrylate (2 EHA) and minor quantities of N-methylol acrylamide (NMA) and acrylic acid (AA), the latter two being the same for all copolymers, with results as shown in the following table:

| Copolymer Composition | 42 parts BuAcr 52 parts VAc Small amounts of NMA and AA 0 parts 2 EHA | 38 parts BuAcr 47 parts VAc Small amounts of NMA and AA 9 parts 2 EHA | 35 parts BuAcr 43 parts VAc Small amounts of NMA and AA 17 parts 2 EHA |
|---|---|---|---|
| Weight (g/yd$^2$) of sheet | 19.5 | 18.5 | 17.8 |
| Strike through (sec) | 1.4 | 1.8 | 1.8 |
| Dryness (g) | 1.6 | 1.0 | 0.6 |

Other sheets were made by impregnating a polyester fiber web with binders that are copolymers of ethylacrylate (Ethylacr.), 2-ethyl hexyl acrylate (2-EHA) and minor quantities of acrylic acid (AA) and N-methylol acrylamide (NMA), the latter two being the same for both copolymers, with results as set forth in the following table:

| Composition of Copolymer | 92 parts Ethylacr Small amounts of AA and NMA No EHA | 80 parts Ethylacr Small amounts of AA and NMA 15 2-EHA |
|---|---|---|
| Weight (g/yd$^2$) | 17.8 | 18.8 |
| Strike through (sec) | .98 | 3.5 |
| Dryness (g) | .47 | .16 |

Similar results can be obtained by employing other polymeric binders containing amounts of combined 2-ethyl hexyl acrylate within the range specified above.

What is claimed is:

1. In a disposable diaper having a water-resistant backing sheet, a layer of absorbent material, and a top sheet arranged to be placed in contact with the skin, the improvement comprising a top sheet having a fibrous textile web impregnated with a polymeric binder in which at least 1% by weight of the binder consists of combined 2-ethyl hexyl acrylate.

2. A disposable diaper as claimed in claim 1 in which said binder is at least 15% by weight of the total top sheet including fibrous web.

3. A disposable diaper as claimed in claim 1 or 2 in which binder comprises a blend of (1) a copolymer of an alkyl acrylate in which the alkyl group contains from 1 to 5 carbon atoms with a copolymerizable monomer and (2) a copolymer of 2-ethyl hexyl acrylate with a copolymerizable monomer.

4. A disposable diaper as claimed in claims 1 or 2 in which the amount of combined 2-ethyl hexyl acrylate is from 3 to 30% by weight of the total binder.

5. A disposable diaper as claimed in claim 1 in which said binder is from 20 to 50% by weight of the total top sheet including fibrous web, the amount of combined 2-ethyl hexyl acrylate is from 3 to 30% by weight of the total binder, and the weight of said top sheet is from 10 to 30 grams per square yard.

6. A disposable diaper as claimed in claim 1 in which said binder comprises a copolymer of alkyl acrylates in which the alkyl group contains 1 to 5 carbon atoms and 2-ethyl hexyl acrylate.

7. A disposable diaper as claimed in claim 1 in which said binder comprises a copolymer containing combined alkyl acrylate in which the alkyl group contains 1 to 5 carbon atoms, vinyl acetate, and 2-ethyl hexyl acrylate.

8. A disposable diaper as claimed in claim 1 in which said binder comprises a copolymer containing combined butyl acrylate, vinyl acetate, and 2-ethyl hexyl acrylate.

* * * * *